United States Patent
Ueda

(10) Patent No.: US 9,000,019 B2
(45) Date of Patent: Apr. 7, 2015

(54) AQUEOUS AGROCHEMICAL SUSPENSION COMPOSITION AND AQUEOUS AGROCHEMICAL SUSPENSION FORMULATION

(71) Applicant: Sumitomo Chemical Company, Limited, Tokyo (JP)

(72) Inventor: Nobuhito Ueda, Takarazuka (JP)

(73) Assignee: Sumitomo Chemical Company, Limted, Tokyo (JP)

(*) Notice: Subject to any disclaimer, the term of this patent is extended or adjusted under 35 U.S.C. 154(b) by 0 days.

(21) Appl. No.: 14/351,318

(22) PCT Filed: Nov. 2, 2012

(86) PCT No.: PCT/JP2012/079048
§ 371 (c)(1),
(2) Date: Apr. 11, 2014

(87) PCT Pub. No.: WO2013/065874
PCT Pub. Date: May 10, 2013

(65) Prior Publication Data
US 2014/0235682 A1    Aug. 21, 2014

(30) Foreign Application Priority Data

Nov. 4, 2011   (JP) ................................. 2011-242561

(51) Int. Cl.
*A01N 25/02* (2006.01)
*A01N 25/04* (2006.01)
*A01N 43/76* (2006.01)

(52) U.S. Cl.
CPC ................ *A01N 25/02* (2013.01); *A01N 25/04* (2013.01); *A01N 43/76* (2013.01)

(58) Field of Classification Search
CPC ........... A01N 25/04; A01N 43/76; A01P 7/02
USPC ....................................................... 514/374
See application file for complete search history.

(56) References Cited

U.S. PATENT DOCUMENTS 5,478,855 A   12/1995   Suzuki et al.

FOREIGN PATENT DOCUMENTS

| CA | 2635407 A1 | 12/2008 |
|---|---|---|
| CN | 101697724 A | 4/2010 |
| CN | 101856029 A | 10/2010 |
| CN | 101856034 A | 10/2010 |
| CN | 101884331 A | 11/2010 |
| CN | 101999382 A | 4/2011 |
| CN | 102017960 A | 4/2011 |
| CN | 102210321 A | 10/2011 |
| CN | 102302011 A | 1/2012 |
| CN | 102308809 A | 1/2012 |
| CN | 102308841 A | 1/2012 |
| CN | 102484990 A | 6/2012 |
| EP | 0639572 A1 | 2/1995 |
| JP | 2007-153795 A | 6/2007 |
| JP | 2011-26215 A | 2/2011 |
| JP | 2012-188382 A | 10/2012 |
| WO | WO 93/22297 A1 | 11/1993 |
| WO | WO 2011/092141 A2 | 8/2011 |

OTHER PUBLICATIONS

International Preliminary Report on Patentability, dated May 6, 2014, issued in the corresponding International Application No. PCT/JP2012/079048.
International Search Report, mailed on Jan. 22, 2013, issued in the corresponding International Application No. PCT/JP2012/079048.
Kumiai Nouyaku Souran, Ja Zenno, 2008, pp. 508-509 (including an English translation).
The First Office Action (including an English translation), dated Nov. 15, 2014, issued in the corresponding Chinese Patent Application No. 201280052970.5.

*Primary Examiner* — Raymond Henley, III
(74) *Attorney, Agent, or Firm* — Birch, Stewart, Kolasch & Birch, LLP

(57) ABSTRACT

The present invention provides an agrochemical composition having excellent efficacy, which comprises, as active ingredient, 2-(2,6-difluorophenyl)-4-[4-(1,1-dimethylethyl)-2-ethoxyphenyl]-4,5-dihydrooxazole. The aqueous agrochemical suspension composition comprising 2-(2,6-difluorophenyl)-4-[4-(1,1-dimethylethyl)-2-ethoxyphenyl]-4,5-dihydrooxazole, at least one kind of alcohol selected from the group consisting of ethylene glycol, propylene glycol and glycerin, an inorganic thickener and a dispersant shows excellent efficacy.

20 Claims, No Drawings

AQUEOUS AGROCHEMICAL SUSPENSION COMPOSITION AND AQUEOUS AGROCHEMICAL SUSPENSION FORMULATION

TECHNICAL FIELD

The present invention relates to an aqueous agrochemical suspension composition and an aqueous agrochemical suspension formulation.

BACKGROUND ART

Hereto, 2-(2,6-difluorophenyl)-4-[4-(1,1-dimethylethyl)-2-ethoxyphenyl]-4,5-dihydrooxazole has been known as compound having miticidal activity and agrochemical compositions comprising the same as active ingredient have been put into practical use (see U.S. Pat. No. 5,478,855).

However, the agrochemical compositions comprising the compound as active ingredient do not necessarily exert sufficient efficacy and therefore there has been a desirous of new agrochemical compositions comprising the compound.

SUMMARY OF THE INVENTION

Problems to be Solved by Invention

An object of the present invention is to provide an agrochemical composition having excellent controlling efficacy, which comprises, as active ingredient, 2-(2,6-difluorophenyl)-4-[4-(1,1-dimethylethyl)-2-ethoxyphenyl]-4,5-dihydrooxazole.

Means to Solve Problems

The present inventor has intensively studied to find the agrochemical composition having excellent efficacy, which comprises, as active ingredient, 2-(2,6-difluorophenyl)-4-[4-(1,1-dimethylethyl)-2-ethoxyphenyl]-4,5-dihydrooxazole, and then have found out that an aqueous agrochemical suspension composition comprising 2-(2,6-difluorophenyl)-4-[4-(1,1-dimethylethyl)-2-ethoxyphenyl]-4,5-dihydrooxazole, at least one kind of alcohol selected from the group consisting of ethylene glycol, propylene glycol and glycerin, an inorganic thickener and a dispersant has excellent controlling efficacy, which thus has completed the present invention.

Specifically, the present invention includes the following [1] to [11].
[1] An aqueous agrochemical suspension composition comprising 2-(2,6-difluorophenyl)-4-[4-(1,1-dimethylethyl)-2-ethoxyphenyl]-4,5-dihydrooxazole, at least one kind of alcohol selected from the group consisting of ethylene glycol, propylene glycol and glycerin, an inorganic thickener and a dispersant.
[2] The aqueous agrochemical suspension composition of [1], wherein an amount of the at least one kind of alcohol selected from the group consisting of ethylene glycol, propylene glycol and glycerin is within a range of 2 to 100 parts by weight, an amount of the inorganic thickener is within a range of 2 to 50 parts by weight and an amount of the dispersant is within a range of 2 to 100 parts by weight, as opposed to 100 parts by weight of 2-(2,6-difluorophenyl)-4-[4-(1,1-dimethylethyl)-2-ethoxyphenyl]-4,5-dihydrooxazole.
[3] The aqueous agrochemical suspension composition of [1], wherein an amount of the at least one kind of alcohol selected from the group consisting of ethylene glycol, propylene glycol and glycerin is within a range of 5 to 60 parts by weight, an amount of the inorganic thickener is within a range of 4 to 30 parts by weight and an amount of the dispersant is within a range of 5 to 85 parts by weight, as opposed to 100 parts by weight of 2-(2,6-difluorophenyl)-4-[4-(1,1-dimethylethyl)-2-ethoxyphenyl]-4,5-dihydrooxazole.
[4] The aqueous agrochemical suspension composition of any one of [1] to [3], wherein the inorganic thickener is at least one kind selected from the group consisting of magnesium aluminium silicate and montmorillonite.
[5] The aqueous agrochemical suspension composition of any one of [1] to [4], wherein the dispersant is polyoxyethylene arylphenyl ether phosphate.
[6] An aqueous agrochemical suspension formulation comprising 2-(2,6-difluorophenyl)-4-[4-(1,1-dimethylethyl)-2-ethoxyphenyl]-4,5-dihydrooxazole, at least one kind of alcohol selected from the group consisting of ethylene glycol, propylene glycol and glycerin, an inorganic thickener and a dispersant.
[7] The aqueous agrochemical suspension formulation of [6], wherein an amount of 2-(2,6-difluorophenyl)-4-[4-(1,1-dimethylethyl)-2-ethoxyphenyl]-4,5-dihydrooxazole is within a range of 0.1 to 50 weight %, an amount of the at least one kind of alcohol selected from the group consisting of ethylene glycol, propylene glycol and glycerin is within a range of 0.2 to 10 weight % and an amount of the inorganic thickener is within a range of 0.1 to 5 weight % and an amount of the dispersant is within a range of 1 to 15 weight %, as opposed to the total amount of the formulation.
[8] The aqueous agrochemical suspension formulation of [6] or [7], wherein an amount of the at least one kind of alcohol selected from the group consisting of ethylene glycol, propylene glycol and glycerin is within a range of 2 to 100 parts by weight, an amount of the inorganic thickener is within a range of 2 to 50 parts by weight and an amount of the dispersant is within a range of 2 to 100 parts by weight, as opposed to 100 parts by weight of 2-(2,6-difluorophenyl)-4-[4-(1,1-dimethylethyl)-2-ethoxyphenyl]-4,5-dihydrooxazole.
[9] The aqueous agrochemical suspension formulation of [6] or [7], wherein an amount of the at least one kind of alcohol selected from the group consisting of ethylene glycol, propylene glycol and glycerin is within a range of 5 to 60 parts by weight, an amount of the inorganic thickener is within a range of 4 to 30 parts by weight and an amount of the dispersant is within a range of 5 to 85 parts by weight, as opposed to 100 parts by weight of 2-(2,6-difluorophenyl)-4-[4-(1,1-dimethylethyl)-2-ethoxyphenyl]-4,5-dihydrooxazole.
[10] The aqueous agrochemical suspension formulation of any one of [6] to [9], wherein the inorganic thickener is at least one kind selected from the group consisting of magnesium aluminium silicate and montmorillonite.
[11] The aqueous agrochemical suspension formulation of any one of [6] to [10], wherein the dispersant is polyoxyethylene arylphenyl ether phosphate.

Effect of Invention

The aqueous agrochemical suspension composition of the present invention provides an agrochemical composition having excellent efficacy, which comprises, as active ingredient, 2-(2,6-difluorophenyl)-4-[4-(1,1-dimethylethyl)-2-ethoxyphenyl]-4,5-dihydrooxazole. Also the aqueous agrochemical suspension formulation of the present invention can be diluted with water, if necessary, containing a spreading agent and the like, which thereby is useful for providing the aqueous agrochemical suspension composition of the present invention.

MODE FOR CARRYING OUT THE INVENTION

Hereinafter, the present invention is explained in detail.

An aqueous agrochemical suspension composition of the present invention is a composition characterized by containing 2-(2,6-difluorophenyl)-4-[4-(1,1-dimethylethyl)-2-ethoxyphenyl]-4,5-dihydrooxazole (hereinafter referred to as "Present compound"), at least one kind of alcohol selected from the group consisting of ethylene glycol, propylene glycol and glycerin (hereinafter referred to as "Present alcohol"), an inorganic thickener and a dispersant into water and also suspending the present compound into water.

The present compound as used herein is described in, for example, the description of U.S. Pat. No. 5,478,855 and can be prepared according to the method described in the description.

The present alcohol as used herein is at least one kind of alcohols selected from the group consisting of ethylene glycol, propylene glycol and glycerin, and can be also used as mixture of these alcohols.

In the aqueous agrochemical suspension composition of the present invention, the present alcohol is contained in total thereof within a range of usually 2 to 100 parts by weight and preferably 5 to 60 parts by weight as opposed to 100 parts by weight of the present compound.

The inorganic thickener as used herein includes, for example, a solid fine powder such as magnesium aluminium silicate and montmorillonite(bentonite) and white carbon(hydrophilic silica), and magnesium aluminium silicate and montmorillonite(bentonite) are preferred because of usefulness at adding of small amounts as well as easiness of controlling viscosity. Specific examples include Veegum® R, Veegum® granules, Veegum® F, Veegum® HV granules, Veegum® HS granules, Veegum® K granules, Veegum®PRO, Veegum® D granules, Veegum® ULTRA granules, Veegum® PLUS (all of those as aforementioned are magnesium aluminium silicate, which are manufactured by R.T. Vanderbilt Company Inc.) and the others as well as Kunipia® G, Kunipia® F, Kunigel® V1, Kunigel® V2 (all of those as aforementioned are montmorillonite, which are manufactured by Kunimine Industries Co., ltd.).

In the aqueous agrochemical suspension composition, the inorganic thickener is contained within a range of usually 2 to 50 parts by weight and preferably 4 to 30 parts by weight as opposed to 100 parts by weight of the present compound.

The dispersant as used herein includes, for example, polyoxyethylene arylphenyl ether phosphate, and specific examples include Soprophor® FL (manufactured by Rodia Group.) and Newkalgen® FS-3EG (manufactured by Takemoto Oil & Fat Co., Ltd.).

In the aqueous agrochemical suspension composition of the present invention, the dispersant is contained within a range of usually 2 to 100 parts by weight and preferably 5 to 85 parts by weight as opposed to 100 parts by weight of the present compound.

The aqueous agrochemical suspension composition of the present invention can contain any other additives as well as spreading agents, in addition to the present compound, the present alcohols, the inorganic thickener and the dispersant. The other additives include, for example, surfactants, defoamants, antiseptics, stabilizers, colorants, perfumes and organic thickeners. The spreading agents can be viscous liquid mainly composed of surfactants and includes, for example, Dyne® (manufactured by Sumitomo Chemical Garden Products Inc.). When these other additives and/or the spreading agents are contained in the aqueous agrochemical suspension composition of the present invention, the other additives and the spreading agents are contained in total thereof within a range of usually 2 to 500 parts by weight as opposed to 100 parts by weight of the present compound.

In the aqueous agrochemical suspension composition of the present invention, an amount of the present compound is not particularly limited as long as the present compound becomes in the form of a suspension into water, but an amount of water includes, for example, within a range of 80 to 199,999,900 parts by weight as opposed to 100 parts by weight of the present compound.

An aqueous agrochemical suspension formulation of the present invention is a formulation characterized by containing the present compound, the present alcohol, the inorganic thickener and the dispersant into water and also suspending the present compound into water. The aqueous agrochemical suspension formulation of the present invention can be diluted with water, if necessary, containing the spreading agent and the like to prepare the aqueous agrochemical suspension composition of the present invention.

As opposed to the total amount of the aqueous agrochemical suspension formulation of the present invention, an amount of the present compound is within a range of usually 0.1 to 50 weight % and preferably 1 to 40 weight %, and an amount of the present alcohols is within a range of usually 0.2 to 10 weight % and preferably 1 to 8 weight %, and an amount of the inorganic thickener is within a range of usually 0.05 to 5 weight %, preferably 0.1 to 5 weight % and more preferably 0.1 to 3 weight %, and an amount of the dispersant is within a range of usually 1 to 15 weight % and preferably 2 to 10 weight %.

An amount of water is within a range of usually 20 to 98 weight % as opposed to the total amount of the aqueous agrochemical suspension formulation of the present invention.

The aqueous agrochemical suspension formulation of the present invention can further contain, if necessary, the above-mentioned any other additives. When the other additives are contained in the aqueous agrochemical suspension formulation, an amount of the other additives is within a range of 1 to 10 weight % as opposed to the total amount of the aqueous agrochemical suspension formulation of the present invention.

The aqueous agrochemical suspension formulation of the present invention can be prepared by mixing the present compound, the present alcohols and the dispersant, if necessary, the other additives with water, followed by being subject the resulting mixture to a wet grinding method so as to finely grind the present compound, to prepare a suspension, and then by adding the inorganic thickener or an aqueous solution containing the same to the suspension and further by, if necessary, stirring the resulting mixture so as to make the whole thereof homogenous.

The wet grinding method includes, for example, a method comprising an addition of rigid beads such as glass beads to a mixture solution which is prepared by mixing the present compound, the present alcohols, the dispersant and, if necessary, the other additives with water, followed by an application of the resulting mixture to a wet grinding mill such as wet bead milling (for example, DYNO-MILL®) and sand grinder.

In the aqueous agrochemical suspension formulation of the present invention which is prepared by the above-mentioned process, the present compound is grinded and then dispersed in the form of fine powder into the formulation, and the volume median diameter of the power is within a range of usually 20 μm or less and specifically the extent of 0.5 to 5 μm.

The aqueous agrochemical suspension composition can be used the aqueous agrochemical suspension formulation as itself or with dilution it with water, if necessary, containing the spreading agent.

The aqueous agrochemical suspension composition of the present invention can be applied to an area for cultivating crops or to the crops directly in order to control harmful mites which live in the area for cultivating crops or in the crops. The dose of the aqueous agrochemical suspension composition of the present invention can be set appropriately depending on the generation status of the harmful mites and the like, but the dose includes, for example, within a range of 1 to 1,000 grams and preferably 10 to 100 grams as a dose of the present compound per 1,000 $m^2$ of the area for cultivating crops.

EXAMPLE

The following Preparation Examples including Formulation Examples and Reference Examples as well as Test Examples serve to illustrate the present invention in more detail, which should not intend to limit the present invention.

Formulation Example 1

10.3 Parts by weight of 2-(2,6-difluorophenyl)-4-[4-(1,1-dimethylethyl)-2-ethoxyphenyl]-4,5-dihydrooxazole (purity: 97.0%) is mixed with 2.67 parts by weight of polyoxyethylene arylphenyl ether phosphate (Soprophor® FL (manufactured by Rodia Group.)), 0.33 parts by weight of silicon defoamant (Antiformer C Emulsion®, manufactured by Dow Corning), 5 parts by weight of propylene glycol and 51.03 parts by weight of deionized water, and the resulting mixture was subjected to a wet grinding with DYNO-MILL KDL® (manufactured by Shinmaru Enterprises Corporation) to give a suspension. Separately, 0.23 parts by weight of xanthan gum (Kelzan® S, manufactured by CP Kelco Company), 0.46 parts by weight of magnesium aluminium silicate (Veegum® R, manufactured by R.T. Vanderbilt Company Inc.) and 0.13 parts by weight of antiseptic (Proxel® GXL, manufactured by Arch Chemicals Inc.) were added into 29.85 parts by weight of deionized water and then the resulting mixture was continued to stirring for 1 hour, to prepare a thickener solution. The thickener solution was added to the suspension, followed by mixing the resulting mixture to give the aqueous agrochemical suspension formulation of the present invention.

Formulation Example 2

The same operations were carried out according to the Formulation Example 1 except that ethylene glycol was used in place of propylene glycol to give the aqueous agrochemical suspension formulation of the present invention.

Formulation Example 3

The same operations were carried out according to the Formulation Example 1 except that glycerin was used in place of propylene glycol to give the aqueous agrochemical suspension formulation of the present invention.

Formulation Example 4

10.3 Parts by weight of 2-(2,6-difluorophenyl)-4-[4-(1,1-dimethylethyl)-2-ethoxyphenyl]-4,5-dihydrooxazole (purity: 97.0%), 8.4 parts by weight of polyoxyethylene arylphenyl ether phosphate (Newkalgen® FS-3EG (manufactured by Takemoto Oil & Fat Co., Ltd.), 0.53 parts by weight of silicon defoamant (Pronal® EX-300, manufactured by Toho Chemical Industry Co., Ltd.), 2.63 parts by weight of montmorillonite (Kunipia® F, manufactured by Kunimine Industries Co., ltd.), 0.79 parts by weight of ethylene glycol, 0.21 parts by weight of antiseptic (Proxel® GXL, manufactured by Arch Chemicals Inc.) and 77.14 parts by weight of deionized water were mixed, and the resulting mixture was subjected to a wet grinding with DYNO-MILL KDL® (manufactured by Shinmaru Enterprises Corporation) to give the aqueous agrochemical suspension formulation of the present invention.

Reference Example 1

3.09 Parts by weight of 2-(2,6-difluorophenyl)-4-[4-(1,1-dimethylethyl)-2-ethoxyphenyl]-4,5-dihydrooxazole (purity: 97.0%) was dissolved into 20 parts by weight of aromatic hydrocarbons (Solvesso® 200, manufactured by Exxon Mobil Co.) to prepare an oil phase. Separately, 4 parts by weight of polyvinyl alcohol (Gohsenol® GL-05, manufactured by The Nippon Synthetic Chemical Industry Co. Ltd.), 0.2 parts by weight of silicon defoamant (Antiformer C Emulsion®, manufactured by Dow Corning), 5 parts by weight of propylene glycol and 49.04 parts by weight of deionized water to prepare an aqueous phase. To the aqueous phase was added dropwise the oil phase under stirring the aqueous phase with T.K. autohomomixer (manufactured by Tokushu Kika Kogyo Co., Ltd.) to prepare an emulsion. Next, 0.14 parts by weight of xanthan gum (Kelzan® S, manufactured by CP Kelco Company), 0.28 parts by weight of magnesium aluminium silicate (Veegum® R, manufactured by R.T. Vanderbilt Company Inc.) and 0.2 parts by weight of antiseptic (Proxel® GXL, manufactured by Arch Chemicals Inc.) were added into 18.05 parts by weight of deionized water and then the resulting mixture was continued to stirring for 1 hour, to prepare a thickener solution. The thickener solution was added to the emulsion, followed by mixing the resulting mixture to give the emulsified concentrate.

Reference Example 2

The same operations were carried out according to the Formulation Example 1 except that deionized water was used in place of propylene glycol to give the aqueous agrochemical suspension formulation.

Next, the Test Examples are shown below.

Test Example 1

The formulations obtained in the above-mentioned Formulation Examples and the Reference Examples were diluted with appropriate amounts of water so that the concentration of 2-(2,6-difluorophenyl)-4-[4-(1,1-dimethylethyl)-2-ethoxyphenyl]-4,5-dihydrooxazole was 0.5 ppm.

A leaf of kidney bean was punched out to 2 cm in diameter to prepare a leaf disk. The leaf disk was placed on absorbent cotton moistened with water, so that the upper side of the leaf was in an upward direction. To the leaf was applied the diluted solution obtained above with a spreader (manufactured by Daiki Co. Ltd.) so as to be 3.5 mg/$cm^2$ of an adhesion amount.

Thereafter, 10 adult female two-spotted spider mites (*Tetranychus urticae*) were inoculated onto the leaves. At 1 day after the inoculation, the adult female spider mites were removed and the leaf disk was placed at 25° C. in a room.

At 7 days after the removal of adult female spider mites, the number of unhatched eggs and the number of the hatched larvae including the life and death thereof were examined.

The miticidal ratio was calculated by the following equation 1. The results are shown in Table 1.

Miticidal ratio (%)=(the number of unhatched eggs+ the number of dead hatched larvae)/(the number of unhatched eggs+the number of dead hatched larvae+the number of live hatched larvae)×100   [Equation 1]

TABLE 1

| test formulation | Miticidal ratio (%) |
|---|---|
| Formulation Ex. 1 | 98.8 |
| Formulation Ex. 2 | 83.2 |
| Formulation Ex. 3 | 83.3 |
| Formulation Ex. 4 | 100 |
| Reference Ex. 2 | 64.8 |

Test Example 2

The formulations obtained in the above-mentioned Formulation Examples and the Reference Examples were diluted with appropriate amounts of water so that the concentration of 2-(2,6-difluorophenyl)-4-[4-(1,1-dimethylethyl)-2-ethoxyphenyl]-4,5-dihydrooxazole was 1.5 ppm. 50 mL of the diluted solution was applied to the stems and leaves of nursery tree of summer orange (*Citrus natsudaidai*) (breed: Kawanodaidai) that was grown in a pot. After 4 weeks of the application, a leaf of the orange was cut and was then placed on absorbent cotton that was spread in a Petri dish having 9 cm in diameter and moistened with water. 10 Adult female citrus red mites (*Panonychus citri*) were released on the leaf and the Petri dish was left to stand in an artificial climate chamber (air temperature 25, ° C., humidity 70%, light condition: light period 16 hours, dark period 8 hours). After three days, the adult female citrus red mites were removed with the eggs laid on the leaf being left. The Petri dish was left to stand in the artificial climate chamber (air temperature 25° C., humidity 70%, light condition: light period 16 hours, dark period 8 hours) for nine days. The number of hatched larvae of citrus red mites and the number of unhatched eggs were counted and the ovicidal ratio was calculated by the following equation 2. The results are shown in Table 2.

Ovicidal ratio (%)={the number of unhatched eggs/ (the number of larvae+the number of unhatched eggs)}×100   [Equation 2]

TABLE 2

| test formulation | Ovicidal ratio (%) |
|---|---|
| Formulation Ex. 4 | 99.1 |
| Reference Ex. 1 | 21.0 |

The invention claimed is:

1. An aqueous agrochemical suspension composition comprising 2-(2,6-difluorophenyl)-4-[4-(1,1-dimethylethyl)-2-ethoxyphenyl]-4,5-dihydrooxazole, at least one kind of alcohol selected from the group consisting of ethylene glycol, propylene glycol and glycerin, an inorganic thickener and a dispersant.

2. The aqueous agrochemical suspension composition according to claim 1, wherein an amount of the at least one kind of alcohol selected from the group consisting of ethylene glycol, propylene glycol and glycerin is within a range of 2 to 100 parts by weight, an amount of the inorganic thickener is within a range of 2 to 50 parts by weight and an amount of the dispersant is within a range of 2 to 100 parts by weight, as opposed to 100 parts by weight of 2-(2,6-difluorophenyl)-4-[4-(1,1-dimethylethyl)-2-ethoxyphenyl]-4,5-dihydrooxazole.

3. The aqueous agrochemical suspension composition according to claim 1, wherein an amount of the at least one kind of alcohol selected from the group consisting of ethylene glycol, propylene glycol and glycerin is within a range of 5 to 60 parts by weight, an amount of the inorganic thickener is within a range of 4 to 30 parts by weight and an amount of the dispersant is within a range of 5 to 85 parts by weight, as opposed to 100 parts by weight of 2-(2,6-difluorophenyl)-4-[4-(1,1-dimethylethyl)-2-ethoxyphenyl]-4,5-dihydrooxazole.

4. The aqueous agrochemical suspension composition according to claim 1, wherein the inorganic thickener is at least one kind selected from the group consisting of magnesium aluminium silicate and montmorillonite.

5. The aqueous agrochemical suspension composition according to claim 1, wherein the dispersant is polyoxyethylene arylphenyl ether phosphate.

6. An aqueous agrochemical suspension formulation comprising 2-(2,6-difluorophenyl)-4-[4-(1,1-dimethylethyl)-2-ethoxyphenyl]-4,5-dihydrooxazole, at least one kind of alcohol selected from the group consisting of ethylene glycol, propylene glycol and glycerin, an inorganic thickener and a dispersant.

7. The aqueous agrochemical suspension formulation according to claim 6, wherein an amount of 2-(2,6-difluorophenyl)-4-[4-(1,1-dimethylethyl)-2-ethoxyphenyl]-4,5-dihydrooxazole is within a range of 0.1 to 50 weight %, an amount of the at least one kind of alcohol selected from the group consisting of ethylene glycol, propylene glycol and glycerin is within a range of 0.2 to 10 weight % and an amount of the inorganic thickener is within a range of 0.1 to 5 weight % and an amount of the dispersant is within a range of 1 to 15 weight %, as opposed to the total amount of the formulation.

8. The aqueous agrochemical suspension formulation according to claim 6, wherein an amount of the at least one kind of alcohol selected from the group consisting of ethylene glycol, propylene glycol and glycerin is within a range of 2 to 100 parts by weight, an amount of the inorganic thickener is within a range of 2 to 50 parts by weight and an amount of the dispersant is within a range of 2 to 100 parts by weight, as opposed to 100 parts by weight of 2-(2,6-difluorophenyl)-4-[4-(1,1-dimethylethyl)-2-ethoxyphenyl]-4,5-dihydrooxazole.

9. The aqueous agrochemical suspension formulation according to claim 6, wherein an amount of the at least one kind of alcohol selected from the group consisting of ethylene glycol, propylene glycol and glycerin is within a range of 5 to 60 parts by weight, an amount of the inorganic thickener is within a range of 4 to 30 parts by weight and an amount of the dispersant is within a range of 5 to 85 parts by weight, as opposed to 100 parts by weight of 2-(2,6-difluorophenyl)-4-[4-(1,1-dimethylethyl)-2-ethoxyphenyl]-4,5-dihydrooxazole.

10. The aqueous agrochemical suspension formulation according to claim 6, wherein the inorganic thickener is at least one kind selected from the group consisting of magnesium aluminium silicate and montmorillonite.

11. The aqueous agrochemical suspension formulation according to claim 6, wherein the dispersant is polyoxyethylene arylphenyl ether phosphate.

12. The aqueous agrochemical suspension composition according to claim 2, wherein the inorganic thickener is at least one kind selected from the group consisting of magnesium aluminium silicate and montmorillonite.

13. The aqueous agrochemical suspension composition according to claim 3, wherein the inorganic thickener is at least one kind selected from the group consisting of magnesium aluminium silicate and montmorillonite.

14. The aqueous agrochemical suspension composition according to claim 2, wherein the dispersant is polyoxyethylene arylphenyl ether phosphate.

15. The aqueous agrochemical suspension composition according to claim 3, wherein the dispersant is polyoxyethylene arylphenyl ether phosphate.

16. The aqueous agrochemical suspension composition according to claim 4, wherein the dispersant is polyoxyethylene arylphenyl ether phosphate.

17. The aqueous agrochemical suspension formulation according to claim 7, wherein an amount of the at least one kind of alcohol selected from the group consisting of ethylene glycol, propylene glycol and glycerin is within a range of 2 to 100 parts by weight, an amount of the inorganic thickener is within a range of 2 to 50 parts by weight and an amount of the dispersant is within a range of 2 to 100 parts by weight, as opposed to 100 parts by weight of 2-(2,6-difluorophenyl)-4-[4-(1,1-dimethylethyl)-2-ethoxyphenyl]-4,5-dihydrooxazole.

18. The aqueous agrochemical suspension formulation according to claim 7, wherein an amount of the at least one kind of alcohol selected from the group consisting of ethylene glycol, propylene glycol and glycerin is within a range of 5 to 60 parts by weight, an amount of the inorganic thickener is within a range of 4 to 30 parts by weight and an amount of the dispersant is within a range of 5 to 85 parts by weight, as opposed to 100 parts by weight of 2-(2,6-difluorophenyl)-4-[4-(1,1-dimethylethyl)-2-ethoxyphenyl]-4,5-dihydrooxazole.

19. The aqueous agrochemical suspension formulation according to claim 7, wherein the inorganic thickener is at least one kind selected from the group consisting of magnesium aluminium silicate and montmorillonite.

20. The aqueous agrochemical suspension formulation according to claim 8, wherein the inorganic thickener is at least one kind selected from the group consisting of magnesium aluminium silicate and montmorillonite.

* * * * *